US012630435B2

(12) United States Patent (10) Patent No.: US 12,630,435 B2
Cicchinelli (45) Date of Patent: May 19, 2026

(54) SYSTEM AND PROCESS FOR THE PRODUCTION OF UAN

(71) Applicant: STAMICARBON B.V., Sittard (NL)

(72) Inventor: Stefano Cicchinelli, Maastricht (NL)

(73) Assignee: STAMICARBON B.V., Sittard (NL)

( * ) Notice: Subject to any disclaimer, the term of this patent is extended or adjusted under 35 U.S.C. 154(b) by 0 days.

(21) Appl. No.: 18/862,384

(22) PCT Filed: Jul. 29, 2024

(86) PCT No.: PCT/NL2024/050422
§ 371 (c)(1),
(2) Date: Nov. 1, 2024

(87) PCT Pub. No.: WO2025/023840
PCT Pub. Date: Jan. 30, 2025

(65) Prior Publication Data
US 2025/0178913 A1 Jun. 5, 2025

(30) Foreign Application Priority Data

Jul. 27, 2023 (EP) ..................................... 23188198

(51) Int. Cl.
| | |
|---|---|
| *C01C 1/18* | (2006.01) |
| *C05C 9/00* | (2006.01) |
| *C07C 273/04* | (2006.01) |

(52) U.S. Cl.
CPC ................ *C01C 1/185* (2013.01); *C05C 9/00* (2013.01); *C07C 273/04* (2013.01)

(58) Field of Classification Search
CPC .. C01C 1/185; C01C 1/18; C05C 9/00; C05C 1/02; C05C 9/005; C07C 273/04
See application file for complete search history.

(56) References Cited

U.S. PATENT DOCUMENTS

2011/0229394 A1* 9/2011 Niehues .................. C05C 9/005
422/187
2019/0224610 A1* 7/2019 Higgins ................. B01D 47/10
(Continued)

FOREIGN PATENT DOCUMENTS

| CN | 104086234 A | 10/2014 |
|---|---|---|
| EP | 3323805 A1 | 5/2018 |
(Continued)

OTHER PUBLICATIONS

Thyssenkrupp. Nitrates for Fertilizers and Technical Applications, Industrial Solutions Fertilizer and Syngas Technologies, Dortmund, Germany. n.d. (12 pages).
(Continued)

*Primary Examiner* — Anthony J Zimmer
*Assistant Examiner* — Syed T Iqbal
(74) *Attorney, Agent, or Firm* — Leason Ellis LLP

(57) ABSTRACT
Disclosed is a system for the production of urea ammonium nitrate (UAN), which is particularly suitable for processing relatively small ammonium nitrate waste streams into UAN. The system comprises a concentration for ammonium nitrate, a treatment section which allows recovering and recirculating nitrogen compounds entrained in vapor from the concentration section, and a pH control section allowing to adjust the pH of the processed ammonium nitrate waste stream to the extent necessary.

20 Claims, 4 Drawing Sheets

(56) References Cited

U.S. PATENT DOCUMENTS

2020/0002239 A1* 1/2020 Puci ........................... C05C 9/00
2021/0163305 A1* 6/2021 Wang ...................... C01C 1/185

FOREIGN PATENT DOCUMENTS

| WO | 2016085343 A1 | 6/2016 |
| WO | 2017111585 A1 | 6/2017 |
| WO | 2017111588 A1 | 6/2017 |
| WO | 2021137700 A1 | 7/2021 |

OTHER PUBLICATIONS

International Search Report and Written Opinion in PCT Application No. PCT/NL2024/050422, mailed Oct. 21, 2024 (14 pages).
Meessen, "Urea", Ullmanns, Wiley-VCH Verlag Gmbh & Co. KGaA, 2010 Digital (39 pages).

* cited by examiner

SYSTEM AND PROCESS FOR THE PRODUCTION OF UAN

CROSS-REFERENCE TO RELATED PATENT APPLICATIONS

This application is a U.S. National Stage Application under 35 U.S.C. § 371 of International Patent Application No. PCT/NL2024/050422, filed Jul. 29, 2024, which claims priority to EP 23188198.8, filed Jul. 27, 2023, which are incorporated by reference in their entireties.

FIELD

The invention pertains to the production of a solution of urea ammonium nitrate in water (UAN). Particularly, the invention is directed to a system and method for processing an ammonium nitrate (AN) waste stream into UAN.

BACKGROUND

Urea ammonium nitrate (UAN) is an aqueous solution of urea and ammonium nitrate and is used as fertilizer. A process for producing UAN generally comprises providing an aqueous solution of ammonium nitrate (AN), providing an aqueous solution of urea, and mixing the ammonium nitrate and urea solutions in a UAN production unit, so as to produce urea ammonium nitrate. The ammonium nitrate and the urea can be provided, e.g., by production in separate ammonium nitrate and urea plants, or in corresponding sections of combined or integrated plants. Also, it has been proposed that the ammonium nitrate is provided in part as a byproduct of an acidic ammonia scrubbing unit.

Background art related to sending all or part of a scrubbing liquid used in an acidic ammonia scrubber to a UAN production unit, is known from WO2017/111588 or from WO2017/111585. The set-up disclosed herein, is limited to an integration with urea production. In both documents, additional ammonium nitrate from a separate ammonium nitrate production section is supplied to the UAN production unit. It would be desired to provide a system for the production of UAN that can be applied to largely any ammonium nitrate waste stream. A further desire thereby is to decrease the discharge of emissions, especially ammonia, nitric acid, and ammonium nitrate, and to minimize waste streams and equipment costs. Also, it would be desired to further improve the efficiency of a system such as disclosed in said background art.

The invention also address the handling of acid aqueous ammonium nitrate solutions that result from acidic scrubbing of ammonia-containing off-gas, e.g. from the acid scrubbing of off-gas (waste air stream) from a finishing section of a urea plant.

Various urea production plants and processes are illustrated in Ullmann's Encyclopaedia of Industrial Chemistry, Chapter Urea, 2010. In many urea production processes, the formed urea melt is at least in part subjected to a finishing step where it is transformed into a solid urea product using a cooling gas stream, e.g. cooling air stream, for instance by granulation or prilling. The resulting off gas, i.e. waste air stream, comprises urea dust and $NH_3$, and air. The urea dust and ammonia can be removed from the waste air stream by scrubbing. Many processes use combined urea dust scrubbing and acid scrubbing, giving an aqueous solution comprising urea and ammonium salt. It has been proposed to use such a solution as a liquid fertilizer.

SUMMARY

In order to better address one or more of the aforementioned desires, the invention provides, in one aspect, a system for the production of urea ammonium nitrate (UAN) comprising an inlet for aqueous ammonium nitrate, an inlet for liquid urea, and an outlet for UAN, the system comprising a concentration section configured to subject aqueous ammonium nitrate to evaporation so as to provide concentrated ammonium nitrate and, downstream of the concentration section and in fluid communication therewith, a production section configured to mix concentrated ammonium nitrate and liquid urea so as to produce UAN, wherein the concentration section has a gas outlet for water vapor, said gas outlet preferably being in fluid communication with a treatment section configured to subject water vapor received from the concentration section to scrubbing, said treatment section having an inlet for scrubbing liquid and an outlet for used scrubbing liquid, wherein the outlet for used scrubbing liquid is preferably in fluid communication with an inlet of the concentration section, and wherein the system comprises a pH control section such that the inlet for aqueous ammonium nitrate is in fluid communication with an inlet of the pH control section, wherein the pH control section is configured to subject aqueous ammonium nitrate to pH control, so as to provide a pH-controlled aqueous ammonium nitrate stream, wherein the pH control section has an outlet for the pH-controlled aqueous ammonium nitrate stream in fluid communication with an inlet of the concentration section, in particular the evaporation section.

In another aspect, a process is provided for the production of urea ammonium nitrate (UAN), comprising obtaining a used scrubbing liquid resulting from subjecting an ammonia-containing off-gas to contact with nitric acid in a scrubber; subjecting the used scrubbing liquid to pH control, said pH control comprising determining pH and adjusting pH to the extent necessary so as to be within a range of 2.0 to 4.5 so as to provide a pH-controlled liquid, subjecting said pH-controlled liquid to evaporation so as to obtain a concentrated ammonium nitrate solution and combining said concentrated ammonium nitrate solution and an aqueous urea solution and/or a urea melt so as to obtain a urea ammonium nitrate solution. The process is advantageously, but not exclusively, carried out in the system of the invention.

In a still further aspect, a method is presented for modifying a pre-existing chemical processing unit having an outlet for a waste aqueous ammonium nitrate stream, the method comprising providing a system for the production of urea ammonium nitrate (UAN) as described above, and connecting said system to said chemical processing unit such that the outlet for the waste aqueous ammonium nitrate of the chemical processing unit is in fluid communication with the inlet for aqueous ammonium nitrate of the system for the production of UAN.

US 12,630,435 B2

3

DETAILED DESCRIPTION

Figure 1:
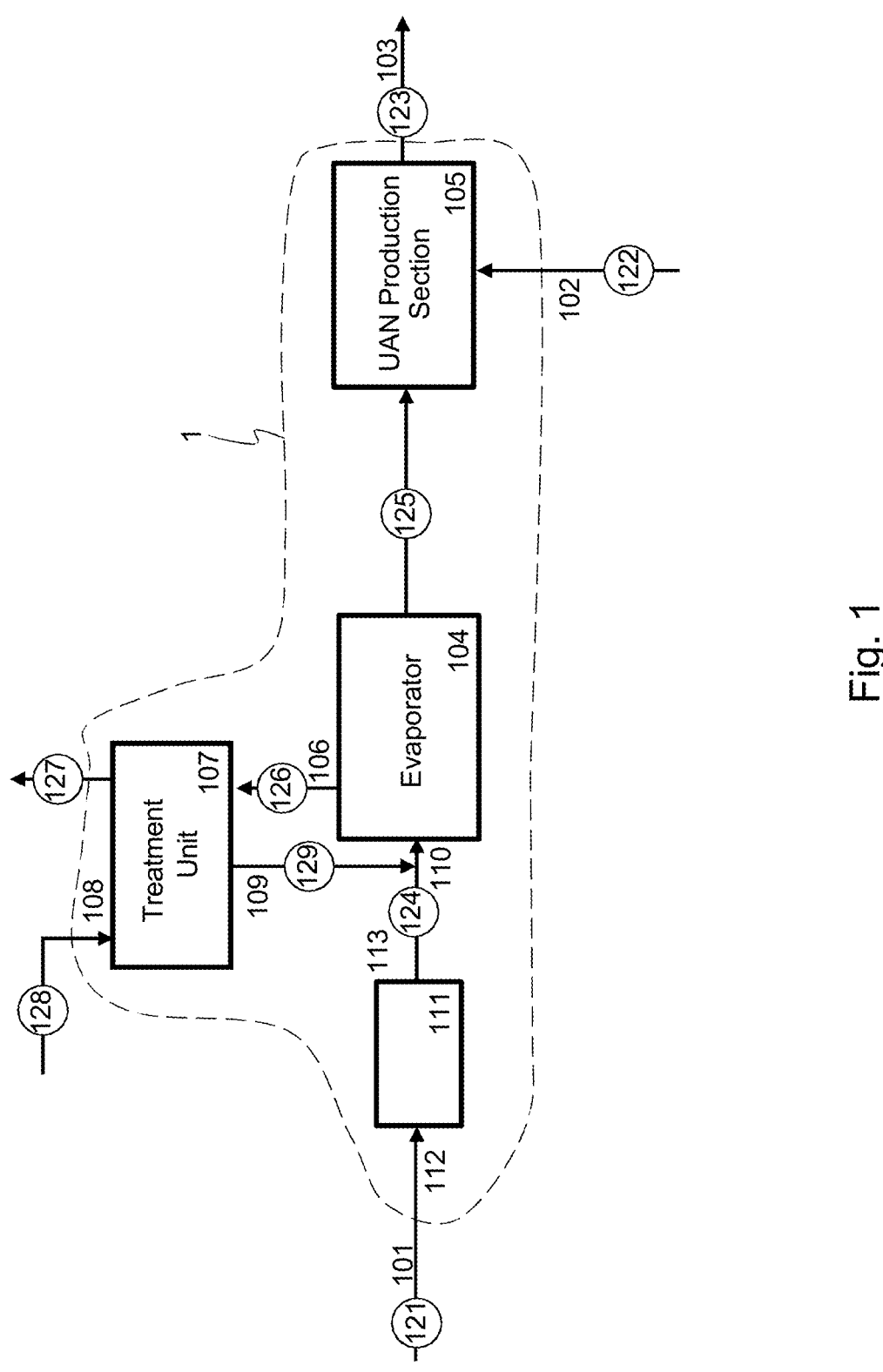
FIG. 1 is a general schematic representation of a system for the production of urea ammonium nitrate (UAN) according to the invention.

Urea Ammonium Nitrate (UAN) is a fertilizer which is generally used as an aqueous solution of urea and ammonium nitrate. Ammonium nitrate is produced by reacting ammonia with a strong solution of nitric acid while maintaining the pH of the solution within narrow boundaries. The resulting solution is then mixed with an aqueous urea solution to obtain UAN. Typical UAN products contain 28 wt. % to 32 wt. % of total nitrogen. The UAN product typically comprises of from 29 wt. % to 38 wt. % urea and of from 36 wt. % to 48 wt. % of ammonium nitrate, with the remainder being water. Preferably the UAN contains max. 35 wt. % water, preferably 20-30 wt. % water. The inventive UAN production process preferably yields such UAN. Hence, the water content of the UAN preferably is not too high. This is especially advantageous for UAN that is used as fertilizer. The invention is based on the judicious insight to conduct the production of UAN on the basis of an acid aqueous ammonium nitrate stream, which is a used scrubbing liquid, that is subjected to pH control, prior to subjecting it to evaporation and mixing it with urea. Preferably, this is done in combination with a treatment step, based on scrubbing, of the vapor from evaporation, preferably with a recirculation step of the liquid from the treatment.

The system disclosed herein, can be put to use in connection with, and can be a part of, any plant from which an acid liquid stream comprising ammonium nitrate is obtained as a by-product or waste stream. Particularly this refers to any such streams that result from subjecting an ammonia-containing off-gas to contact with nitric acid (NA) in a scrubber. The acid aqueous ammonium nitrate stream concerned is thus a used scrubbing liquid, and the stream can also be named 'used scrubbing liquid'. With reference to the fact that the off-gas is a by-product of another chemical reaction, it will be understood that the acid aqueous ammonium nitrate is typically a small waste stream. The present invention seeks particularly to provide a system that is designed for processing such small ammonium nitrate waste streams to UAN. Typically, and in example embodiments of the invention, such small waste streams are in a range of from 1 to 4 Ton/h, such as 2 Ton/h, comprising 5-15 wt. % of ammonium nitrate, typically 10 wt. %, a small amount of nitric acid, typically 0.3-1.0 wt. %, the remainder being water. In an example embodiment, in the event of a urea plant producing a urea melt, the AN waste stream is typically less than 5 wt. %, more typically less than 3 wt. % of the total urea melt produced by such plant. In an embodiment of the process and of the system, the aqueous ammonium nitrate stream comprises 5-15 wt. % of ammonium nitrate, typically 10 wt. %, a small amount of nitric acid, typically 0.3-1.0 wt. %, the remainder being water, and max. 5 wt. % or max 1.0 wt. % urea; this typical composition applying independent of the flow rate. The low level of urea, e.g. only traces of urea, applies in particular if dust scrubbing is used upstream of the acid scrubbing.

This system can be integrated with a chemical processing unit producing an aqueous ammonium nitrate waste stream, typically originating from an acidic ammonia scrubber, such as ammonia plants, ammonium nitrate plants, manure-processing units, composting units, waste processing plants, coke manufacturing plants, urea melt/granulation plants. I.e., the system can be built in into a grass-roots plant comprising an acidic ammonia scrubber. The system can also be built in into a pre-existing plant. Still more advantageously, the system can be provided as a separate unit, that can be connected with any plant for which a useful application is sought for a by-product or waste stream resulting from subjecting an ammonia-containing off-gas to acidic scrubbing.

Such versatile application of the system of the invention is secured by the presence of a judiciously positioned pH control section. This pH control section is positioned such that the inlet for aqueous ammonium nitrate, is in fluid communication with the inlet of the pH control section. I.e., irrespective of whether any further sections, valves, pumps, or other types of equipment are present between the inlet for aqueous ammonium nitrate into the system, the pH-control section is downstream of such inlet and upstream of the evaporation section. The latter is secured with reference to the pH control section having an outlet for the pH-controlled aqueous ammonium nitrate stream in fluid communication with an inlet of the evaporation section.

The pH control section is configured to determine and/or adjust the pH of a stream subjected to such control. Determining pH can involve a pH measurement, or a calculation based on process parameters. Depending on the origin of the acid aqueous ammonium nitrate stream, such calculation can be made in advance, or can be made in situ, such as by a data processing unit receiving input of relevant data related to the scrubbing process from which the acid aqueous ammonium nitrate stream (i.e. the first used scrubbing liquid in FIG. 1) originates. An actual pH measurement of the acid aqueous ammonium nitrate stream can be conducted anywhere in a tract from within the scrubber up to and including inside of the pH control unit. Said pH control secures that the liquid subjected to such control, downstream of the pH control section, has a controlled pH within a desired range, or of a desired value. It will be understood that pH control does not necessarily involve an adjustment of the pH, in the event that the pH of the stream is determined to already have the desired value. In the pH control section, the pH of the aqueous ammonium nitrate liquid is generally controlled at a value in a range of from weak acidic to neutral, generally a pH of from 2.0 to 7.0.

Preferably, with the advantage of preventing the presence of a possible excess of ammonia, the pH is kept at a slightly acidic value, preferably in a range of 2.0 to 4.5. more preferably 2.5 to 3.5, such as at 3.0. This preference applies to the system and to the process. In this way, a high UAN yield is obtained with low NH₃ emissions from the downstream concentrating of the pH-controlled liquid to concentrated AN solution.

The system comprises a concentration section, that is preferably an evaporation section, more preferably is provided by a heater, e.g. a heat exchanger. For instance evaporation by heating with heat exchange with steam is used.

The concentration section is configured to subject an aqueous ammonium nitrate stream, from the pH control section, which is a liquid stream, to evaporation so as to provide concentrated ammonium nitrate, and water vapors, i.e. a separate vapor stream comprising water vapor and entrained ammonium nitrate and nitric acid. The concentration section has an inlet for the pH-controlled aqueous ammonium nitrate, an outlet for the concentrated ammonium nitrate, and an outlet for the water vapors.

The system of the invention comprises a treatment section, which is optional for the process. The treatment section allows recovering and recirculating nitrogen compounds that become entrained in the vapor that results from concentrating the pH-controlled aqueous ammonium nitrate stream by evaporation. This feature serves to prevent unwanted emissions of nitrogen compounds, particularly originating from nitric acid and ammonia entrainments, into the air, in an embodiment wherein the concentration section has a fluid communication with an outlet, such as a stack, for water vapor, e.g, wherein the cleaned vapor from the treatment section is vented.

The vapor typically contains entrained ammonium nitrate (e.g. in the range 0.05-0.2 wt. % AN) and nitric acid (e.g. 0.05-0.2 wt. % NA); with nitric acid typically being gaseous (vapor).

The treatment section is also useful in an embodiment wherein the water vapors after the treatment are condensed and at least a portion of the condensate thereby obtained can be recirculated or otherwise transferred within a plant, rather than being directly vented. Advantageously, such recirculation can be to the treatment section as a treatment liquid for scrubbing off nitric acid and ammonium nitrate entrainments. It will be understood that also with a view to condensation and recirculation, it will generally be undesirable to have nitrogen compounds present in the vapor.

Figure 2:
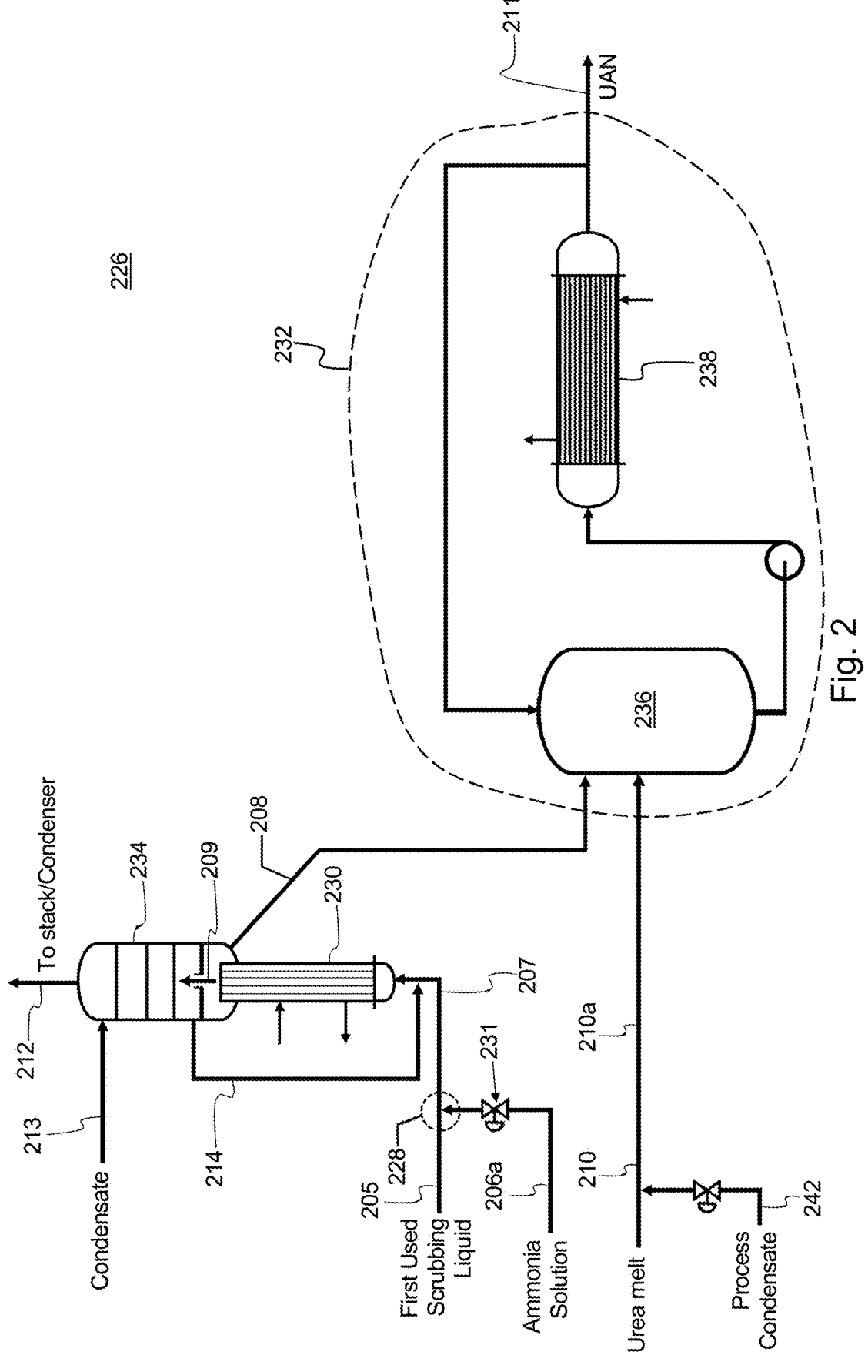
FIG. 2 and FIG. 3 both illustrate a process flow diagram for non-limiting examples of a UAN plant of the invention.

The treatment section is configured to subject the water vapor received from the concentration section (e.g. evaporation section) to scrubbing with a treatment liquid, also called scrubbing liquid (first scrubbing liquid in FIGS. 1 and 2). To this end, the treatment section has an inlet for treatment liquid (scrubbing liquid), and an outlet for used treatment liquid. It will be understood that the treatment liquid will typically be an aqueous liquid stream, e.g. water, e.g. provided as condensate, for instance as steam condensate, e.g. with pH of at least 6, for instance pH 6 to 8. The amount of treatment liquid is e.g. at least 10 wt. % of the acid aqueous ammonium nitrate stream, e.g. in the range 10-30 wt. %.

The treatment section advantageously enables recirculating recovered nitrogen (notably ammonium nitrate and nitric acid) to the UAN production process. To this end, the treatment section has preferably an outlet for used treatment liquid that is in fluid communication with an inlet of the concentration section. Accordingly, recovered nitrogen will be added, as an aqueous used scrubbing liquid, preferably to the pH-controlled ammonium nitrate stream upstream of the concentration section. The treatment section can be referred to as a scrubber, and is e.g. a trayed column scrubber; other types of scrubbers are also possible.

The treatment section is distinct from and separate to any acid scrubber that is used for scrubbing off-gas (waste air) from a urea plant finishing sections giving in a preferred embodiment the acid aqueous ammonium nitrate stream; and the compositions of the gas streams are different. Furthermore, preferably the treatment section uses a treatment liquid that is not acid, preferably has a pH in the range 6 to 8.

The treatment section also has an outlet for cleaned vapor. The system may comprise a condenser connected to receive said cleaned vapor. The condenser comprises an outlet for uncondensed gas and an outlet for condensate. The system may comprise a liquid flow line to supply said condensate at least in part to an inlet of the treatment section.

The presence of the pH control section, and particularly the judicious positioning thereof upstream of the concentration section, provides, as one advantage, a beneficial synergistic effect with the presence of the treatment section, and particularly the recirculation of used treatment liquid therefrom in a preferred embodiment to an inlet of the concentration section. This recirculation would normally result in acid build-up within either or both of the treatment section and the evaporation section. By allowing pH-control of the liquid to be evaporated upstream of the concentration section, at any point in time the presence of acid can be counteracted by allowing the recirculated treatment liquid to be taken up into a less acidic aqueous ammonium nitrate stream.

The pH adjustment also advantageously avoids a decrease of the thermal stability of the ammonium nitrate, thus preventing the ammonium nitrate from becoming prone to decomposition at lower temperatures, which evidently adds to the safety of the process. The pH adjustment, in particular pH increase to less acidic pH, provides the advantage of a reduced risk of AN decomposition in the heating of the concentration section.

This advantage of the pH control step is obtained both in embodiments wherein the used treatment liquid is supplied to the inlet of the concentration section and in embodiments wherein the used treatment liquid is supplied directly to the UAN production section.

The used aqueous treatment liquid, containing water, ammonium nitrate and nitric acid, and resulting from scrubbing water vapor (i.e. the vapor stream from the concentration section) in the treatment section is preferably merged (e.g. combined) with the pH-controlled ammonium nitrate stream, or with the concentrated ammonium nitrate stream, i.e., downstream (for liquid) of the pH-control section. Preferably, said aqueous treatment liquid is recycled back to the inlet of the concentration section (which is preferably an evaporation section).

Recycling the treatment liquid back to the inlet of the concentration section provides as an advantage that the appropriate water balance is achieved for making UAN, i.e. sufficiently low water content of the UAN, with an advantageous relatively low temperature of the evaporation section and with advantageously a relatively high amount of treatment liquid in the treatment section.

Generally, in the event that pH control results in adjusting the pH, such adjustment can be beneficial be to prevent the aforementioned acid build-up, without being limited to that purpose. Accordingly, such pH adjustment involves the addition of base. With a view to the production of UAN, the base will typically be ammonia.

As a general preference, the pH control involves adjusting the pH, in particular increasing the pH by adding a base, in particular by adding ammonia. Adding ammonia as pH adjustment provides the above-discussed advantage regarding thermal stability of the ammonium nitrate, advantages during the evaporation, and contributes to the UAN solution having a desired pH close to 7.

Hence, in a preferred embodiment, the pH control involves adding a base, more preferably ammonia, even more preferably aqueous ammonia solution. Preferably, the pH-control step involves introducing an aqueous ammonia solution, preferably a dilute aqueous ammonia solution comprising ammonia, in an amount of 5 wt. % or less ammonia. Preferably the pH control section is configured for such a step. Preferably the pH control section comprises an inlet for introducing such solution, and a mixing zone (which may include a static mixer and/or active mixer and is e.g. a tie-in point). The system of the invention, as said, preferably is suitable for the conversion of any by-product or waste stream comprising ammonium nitrate, in particular aqueous ammonium nitrate. This generally relates to relatively small streams, or in any event aqueous ammonium nitrate streams of relatively low ammonium nitrate concentrations. In an example embodiment, the aqueous ammonium nitrate stream comprises, typically 5-20 wt. % of ammonium nitrate, more typically 5-15 wt. % of ammonium nitrate, and water, e.g. at least 80 wt. % water. The aqueous ammonium nitrate stream typically also comprises nitric acid, e.g. 0.1-0.5 wt. % nitric acid relative to the total stream. The aqueous ammonium nitrate stream preferably less than 5 wt. % urea, preferably less than 1.0 wt. % urea, e.g. only traces of urea. Traces of urea in the off-gases can remain in processes with dust scrubbing of waste air from urea finishing upstream of a waste air stream upstream of acid scrubbing. These example compositions apply also to the inventive process.

Such aqueous ammonium nitrate streams may originate, e.g., from acid scrubbing with nitric acid of a waste air stream comprising $NH_3$ from a urea finishing sections where a urea melt is solidified into a solid urea product using cooling air (e.g. a granulator or prilling tower); other sources are also possible.

The entrained nitrogen, notably ammonia nitrate and nitric acid, in the water vapors resulting from subjecting such small aqueous ammonium nitrate streams to evaporation, in particular by heating, will have a correspondingly low concentration in the water vapors. The impact hereof, though, can be substantial. Even a small increase in the nitric acid content has a large impact on pH, and if small amounts or nitric acid continue to be processed, this can result an undesirable acid build-up. Moreover, the impact on safety is substantial, taking into account the aforementioned safety hazards resulting from a decreased decomposition temperature of ammonium nitrate. In an absolute sense, however, the amounts of nitric acid to be neutralized are low, in particular the amounts of nitric acid to be neutralized in the pH control section are small, at least relative to the total aqueous ammonium nitrate stream. As mentioned below, this brings about an additional process challenge Thus, generally the amount of ammonia to be added to adjust the pH of the aqueous ammonium nitrate stream in the pH control section is small. For example, 2.3 kg/h of ammonia (i.e. 2.3 kg/h $NH_3$) would need to be added to a 2000 kg/h stream of 10 wt. % aqueous ammonium nitrate that contains 8 kg/h of nitric acid.

With such relatively low amounts of base needed, the flow rate of the base added upon pH-adjustment, is too low for allowing it to be regulated by a standard industrial valve. Whilst this can be solved by applying a small-scale laboratory-type valve, this has drawbacks. E.g., the valve needs to be placed in a specially designed cabinet to be protected against harsh environment. Also, the valve needs to be positioned very close to the line carrying the aqueous ammonium nitrate, which in practice is more difficult to accomplish in the case of a non-industrial type, typically small, valve. In the system of the invention, it is therefore desired to apply a regular, industrial-type valve, e.g. an at least 1 inch valve.

Preferably, the pH-control section is configured for introducing an aqueous ammonia solution, preferably a dilute solution comprising ammonia in an amount of at most 5 wt. % of ammonia, preferably between 0.5 and 5 wt. % of ammonia, most preferably 0.5 to 2 wt. %, into the aqueous ammonium nitrate stream. This provides the advantage, generally, that the aqueous ammonia solution has a relatively larger volume and can be more easily combined, in particular mixed, with the aqueous ammonium nitrate stream, to ensure optimum and homogeneous neutralization of the unreacted nitric acid in the aqueous ammonia solution, e.g. with a regular, industrial-type valve.

With reference to the pH control section as discussed above, it will be understood that the pH control is for instance implemented as a feedback control system or a feed forward system. In a feed forward system, process data and mass balance can be used to determine the pH and adjust it, as necessary based on the determined pH. Dilute ammonia solution is then preferably added downstream of the pH determination location. In a feedback system, pH can be measured downstream of the pH control section and feedback the info to the control section to adjust the pH as necessary. Here, the introduction of dilute ammonia is in fact upstream of the location of pH determination.

The system comprises a production section configured to mix concentrated ammonium nitrate and liquid urea so as to produce UAN, i.e. a UAN production section. The UAN production section is for example connected with the acidic ammonia scrubber of the chemical processing unit and pH control section as only sources of ammonium nitrate in the produced UAN.

In another aspect, the invention provides a process for the production of urea ammonium nitrate (UAN). The process is for example, but not exclusively, carried out in the system of the invention.

As a starting material to this process, an acid aqueous ammonium nitrate stream is provided, that results from subjecting an ammonia-containing off-gas, that preferably contains air, to scrubbing with nitric acid. The acid aqueous ammonium nitrate stream can also be referred to as a used scrubbing liquid and corresponds to the first used scrub liquid in FIG. 1.

The process can be described alternatively as a process for converting an acid aqueous ammonium nitrate stream that results from subjecting an ammonia-containing off-gas to scrubbing with nitric acid, into UAN. The process preferably comprises the step of scrubbing the ammonia-containing off-gas with nitric acid; the process then can alternatively be described as a process for acid scrubbing of an ammonia-containing off-gas stream using nitric acid scrub liquid with the production of UAN from the acidic ammonium nitrate solution resulting from said acid scrubbing.

In the scrubbing with nitric acid, the resulting cleaned off-gas and the acid aqueous ammonium nitrate stream are provided as separate streams. Hence, the acid scrubber has an outlet for vapor (cleaned off-gas) and a separate liquid outlet for acid aqueous ammonium nitrate stream. The acidic scrubber is configured for gas/liquid separation, e.g. by the gas outlet being at an upper part and the liquid outlet being at a lower part. The acid scrubbing is based on the countercurrent contact of gas and nitric-acid containing liquid, typically with gas flowing up and liquid flowing down, for instance with off-gas containing air and $NH_3$.

This acid aqueous ammonium nitrate stream is distinct from the used treatment liquid from the treatment section; these are two different streams and having a different composition.

The process of the invention comprises obtaining the acid aqueous ammonium nitrate stream resulting as a used scrubbing liquid resulting from subjecting an ammonia-containing off-gas to contact with nitric acid in a scrubber to form ammonium nitrate.

The process in an embodiment comprises providing an ammonia-containing off-gas and scrubbing the off-gas with nitric acid in a scrubber thereby forming the acid aqueous ammonium nitrate stream, and a cleaned gas stream, in particular in an acid scrubber. The acid scrubber is for example operated at a pressure below 1.5 bar absolute, for instance at slight under pressure (0.8-1.0 bar absolute).

The process in an embodiment comprises subjecting a urea melt to solidification in a finishing section, e.g. a granulator or prilling tower, using cooling air to provide a solid urea product and a waste air stream comprising urea dust and NH$_3$ and supplying the waste air stream, preferably after dust scrubbing, as at least part of said off-gas processed in said scrubber.

The process in a preferred embodiment comprises subjecting the waste air stream to dust scrubbing to remove at least part, e.g. at least 90 wt. %, of the urea dust from it, and supplying the waste air stream from said dust scrubber to said acid scrubber. The dust scrubbing uses, e.g. a circulating urea solution with aqueous make-up scrub liquid. Hence, preferably, the process comprises dust scrubbing of the waste air stream in a dust scrubber to remove urea dust, and acid scrubbing of the dust-scrubbed waste air stream in a separate acid scrubber with nitric acid to give the acid aqueous ammonium nitrate stream with a low urea content. In the invention, urea solution is added in the UAN production step. Thereby, judiciously the risk of urea degradation by nitric acid is reduced compared to processes wherein combined dust and acid scrubbing is used wherein the used scrub liquid contains urea, ammonium salt, and unreacted acid.

The acid aqueous ammonium nitrate stream comprises, for example, 5 to 50 wt. % ammonium nitrate, e.g. 5-20 wt. % of ammonium nitrate, preferably 5-15 wt. % of ammonium nitrate, and water, e.g. at least 80 wt. % water; and preferably less than 5 wt. % urea, or even less than 1.0 wt. % urea, such as only traces urea. The acid aqueous ammonium nitrate stream also comprises nitric acid and typically also comprises nitric acid, e.g. 0.1-0.5 wt. % nitric acid relative to the total stream. This composition applies e.g. at the inlet of the pH control step.

The pH of the acid aqueous ammonium nitrate stream is e.g. less than 3.0, or less than 2 or less than 1.5. Acid scrub at low pH advantageously may provide for lower gaseous NHs emissions from the waste air stream.

The acid aqueous ammonium nitrate stream is supplied e.g. at atmospheric pressure (1.0 bar absolute).

It will be understood that the acid aqueous ammonium nitrate stream, comprises ammonium nitrate but is not itself directly suitable for the production of UAN. For instance, given the above example compositions of the aqueous ammonium nitrate stream and the UAN product in terms of water content, and even assuming that the urea is supplied to the UAN production section as urea melt, a need to concentrate the aqueous ammonium nitrate stream, i.e. to reduce the water content thereof, remains, at least in embodiments wherein the UAN is produced without addition of extra AN. These embodiments are advantageous in that no separate AN production section is necessary, i.e. no AN neutralizer.

In conformity with one or more of the desires that the invention seeks to address, the used scrubbing liquid, used as the acid aqueous ammonium nitrate stream, can originate from any plant or process that, at some point, involves subjecting an ammonia-containing off-gas to scrubbing with nitric acid. As said, examples hereof are ammonia plants, ammonium nitrate plants, manure-processing units, composting units, waste processing plants, coke manufacturing plants, a urea production plant, e.g. a urea melt/granulation plants, without this summing up being limiting. The urea production plant may comprise a urea finishing section; the urea finishing section is e.g. a granulator.

In a preferred embodiment of the system, the inlet for acid aqueous ammonium nitrate is in fluid communication, e.g. by a liquid flow line, with an outlet for a waste aqueous ammonium nitrate stream (e.g. liquid stream) of a chemical processing unit that comprises an acidic ammonia scrubber producing said waste aqueous ammonium nitrate. The acidic ammonia scrubber is configured for scrubbing a gas stream with a scrub liquid comprising nitric acid and water.

In an embodiment, the system comprises the chemical processing unit, and in particular the acidic ammonia scrubber. In an example embodiment, the chemical processing unit is a urea finishing section, for instance a granulator or prilling tower for solidifying urea melt. As an example, in urea finishing section, a urea melt is solidified into a solid urea product, using a cooling gas (air) stream in case of granulation or a prilling tower, giving a waste air stream that contains gaseous NH$_3$ and urea dust; the NH$_3$ resulting at least in part from a side-reaction in the finishing step. Urea dust is removed from the waste air stream for instance in a dust scrubbing step, with the gas from the dust scrubbing step sent to an acid scrub step using dilute nitric acid as scrub liquid. The acid scrub typically also uses aqueous make-up liquid. Such acid scrubbing step results in an AN solution with unreacted nitric acid, e.g. with low pH, and with a relatively low AN content, which is the acid aqueous ammonium nitrate stream. The process of the invention can comprise the corresponding steps of providing the acid aqueous ammonium nitrate stream from such a chemical processing unit.

In an embodiment, the system comprises the chemical processing unit, which comprises the urea production plant and the finishing section, wherein the finishing section comprises the acidic ammonia scrubber.

In the inventive process, the acid aqueous ammonium nitrate stream is concentrated, preferably by water evaporation by heating the solution. The step of concentrating such an acidic stream will inevitably bring about corrosivity, especially if the concentration is performed by evaporation by heating, which can be detrimental to a plant (e.g. to the equipment), or otherwise will require investments in expensive corrosion-resistant equipment. Also, as mentioned before, the low pH of the solution has an accelerating effect on possible thermal decomposition of ammonium nitrate, which comes with safety issues.

The process of the invention comprises subjecting the acid aqueous ammonium nitrate stream, to pH control, said pH control comprising determining pH and adjusting pH to the extent necessary so as to be within a range of 2 to 4.5 so as to provide a pH-controlled liquid.

A moderate acidic pH of the pH-controlled liquid advantageously reduces or prevents NH$_3$ emissions through the vapor of the concentration step.

In a preferred embodiment, the pH control is pH adjustment, in particular pH increase, and comprises adding an aqueous ammonia solution to the acid aqueous ammonium nitrate stream to increase the pH, thereby giving a pH-adjusted liquid as said pH-controlled liquid. It is possible that the pH increase step is applied at intervals or intermittently, e.g. in case of variations in the pH of the acid aqueous ammonium nitrate stream. The pH adjustment can also be applied continuously.

For example, the pH of the acid aqueous ammonium nitrate stream may be in a range of, e.g. 0.5 to 1.8 based on its nitric acid content before the pH adjustment, and is e.g. above 2.0 after the pH adjustment.

The process comprises subjecting said pH-controlled liquid to evaporation so as to obtain a concentrated ammonium nitrate solution; preferably the evaporation is by heating the solution. This concentrated solution generally has a concentration of at least 60 wt. % of ammonium nitrate, preferably 65 to 85 wt. % of ammonium nitrate, more preferably 70 to 80 wt. %; and contains generally max. 40 wt. % water, or max 20 wt. % water. The evaporation is e.g. carried out in the concentration section of the system. The evaporation is e.g. done by heating in a heat exchanger using steam, preferably LP steam of e.g. 3-5 bar. The use of LP steam is advantageous for process efficiency and for safety reasons regarding the thermal stability of AN.

In an example embodiment, the ammonium nitrate concentration of the ammonium nitrate stream is increased by the water removal by evaporation from an initial concentration in the range 5-20 wt. % to a concentration after the evaporation in the range of 50-90 wt. %, preferably 65 to 85 wt. % of ammonium nitrate, more preferably 70 to 80 wt. %, preferably by evaporation by heating.

Thereupon, in the actual production of UAN, the process comprises combining said concentrated ammonium nitrate solution and a urea-containing liquid stream, preferably an aqueous urea solution and/or a urea melt, so as to obtain a urea ammonium nitrate solution (UAN).

Advantageously the product UAN solution can have the desired low water content by combining the concentrated AN solution with a liquid stream having a sufficiently high urea content.

As a general preference, the formed UAN has a pH in the range 6.5-7.2 (measured at 20° C.). A pH of 6.5-7.2 is typical for UAN-32 and can be useful for storage of the UAN solution. Hence, as a general preference, when the pH control step is to give a pH controlled liquid with pH 2-4.5, followed by concentration, the UAN production step comprises further pH increase to a pH of at least 6.5, more preferably to pH in the range 6.5-7.2. The pH increase can be conducted e.g. by adding a separate ammonia-containing stream, e.g. an aqueous ammonia solution, or by the urea-containing-liquid stream containing ammonia.

Furthermore, preferably the urea-containing liquid stream contains some $NH_3$, e.g. by originating from the evaporation section of the urea plant, which can be advantageous to completely neutralize the concentrated AN (e.g. when the pH control step is to pH 2-4.5) and to produce UAN product with a desired pH of e.g. 6.5-7.2 at 20° C. . . .

Preferably, at least 90 wt. % of the ammonium nitrate in the UAN originates from the acid aqueous ammonium nitrate stream; preferably at least 90 wt. % of the ammonium nitrate in the UAN originates from the pH controlled liquid; more preferably all or substantially all of the ammonium nitrate originates from said streams. Thereby advantageously no separate ammonium nitrate (AN) needs to be added, such that no separate AN neutralizer is necessary. Preferably, at least 90% of the urea in the UAN, preferably all, is added to the AN downstream of the evaporation step (or concentration section), e.g. in the UAN production step. This provides the advantage that the urea is not subject to aggressive conditions in the AN concentration step (low pH, high temperature) where urea may be degraded and biuret formation can occur.

The urea solution and/or a urea melt used in the UAN production typically originates from a urea production process carried out in a urea production plant. Urea is generally produced in such a process from ammonia and carbon dioxide. It can be prepared by introducing an ammonia excess together with carbon dioxide at a pressure between 12 and 40 MPa and at a temperature between 150° C. and 250° C. into a urea synthesis section of the urea production plant. Typical urea production plants further comprise a recovery section and a finishing section. In the recovery section non-converted ammonia and carbon dioxide are recovered and recirculated to the synthesis section. The recovery section is generally followed by an evaporation section. Therein the urea concentration is further increased by the evaporation of water, resulting in a highly concentrated solution that is generally referred to as a urea melt. In the finishing section, typically, the urea melt is brought into a desired solid, particulate form, generally involving techniques such as prilling, granulation, or pelletizing. Such solid urea can be subjected to melting and/or dilution in order to obtain a urea melt or solution as desired. Preferably, the system of the present invention is connected to a urea production plant such that the inlet for liquid urea is in fluid communication with an outlet for liquid urea from a urea plant. This can be from various sections, yielding various urea concentrations.

In preferred embodiments of the system and process, a first part of the urea melt formed in the urea production plant is used to produce solid urea product, and a second part is used for said production of UAN, wherein the UAN production uses AN originating at least in part, e.g. for at least at least 90 wt. %, from the acid scrubbing, with nitric acid, of an ammonia-containing off-gas from the urea production, e.g. from the acid scrubbing waste air stream from the solidification of the first part to of the urea melt into the solid urea product in a finishing section which uses cooling air, e.g. a granulator or a prilling tower.

In an example embodiment, the system respectively the UAN production step receives urea-containing liquid from the evaporation section of the urea plant. In the process, the concentrated ammonium nitrate solution is combined with an aqueous urea solution and/or a urea melt; said aqueous urea solution and urea melt may originate, e.g., from the evaporation section.

The UAN production unit is often located at some distance from the urea melt plant, e.g. at some distance from the evaporation section thereof. In a preferred embodiment of the process, a part of a urea melt containing at least 90 wt. % urea (including biuret) or at least 95 wt. % thereof, is diluted to form a diluted urea liquid stream by adding an aqueous stream and the resulting diluted urea liquid stream is combined with the concentrated AN solution for making the UAN. Preferably, the diluted urea liquid stream is transported to the UAN production unit, e.g. over at least 10 m, or at least 50 m in a transport line to the UAN production. Preferably the diluted urea liquid stream has a concentration of 60-85 wt. % urea (including biuret), more preferably 70-85 wt. % urea, or even 75-85 wt. %, in particular during the transport to the UAN production. Preferably, such a stream is transported to the UAN production unit at a temperature below 135° C. or below 130° C. The relatively low temperature reduces undesired biuret formation in the transport line.

It is noted that the diluted urea liquid stream should have a sufficiently high concentration to permit the production of UAN with the target urea concentration when combined with the concentrated ammonium nitrate solution, preferably when combined with only the concentrated ammonium nitrate solution. Moreover, it is desired that evaporation step in the AN concentration section is performed at moderate temperatures. Therefore, the diluted urea liquid stream preferably comprises at least 70 wt. % urea or at least 75 wt. % urea. Furthermore, the diluted urea liquid stream, originating from the evaporation section, typically contains some $NH_3$, which is beneficial for optimizing the pH of the UAN product.

Typically, a urea production plant will comprise a recovery section from which a urea solution is obtained, e.g. with 70-90 wt. % urea and 10-30 wt. % water, and downstream thereof an evaporation section in which such solution is subjected to concentration. This concentration will preferably occur to the extent that a highly concentrated urea solution is formed (e.g., having more than 90 wt. % of urea, such as more than 95 wt. % of urea, such as more than 99 wt. % of urea) for which the term "urea melt" is used in the art. Typically, the urea solution is concentrated in an evaporation section to a urea melt having a final moisture content of 0.03-5.0% by weight.

In a preferred embodiment of the process, the step of obtaining the acid aqueous ammonium nitrate stream comprises:

Producing urea melt in a urea production plant comprising a synthesis section, a recovery section, an evaporation section, a condensation section, and a waste water treatment section, in particular by:

Reacting $CO_2$ and $NH_3$ to form a urea solution in the synthesis section;

Treating the urea solution from the synthesis section in the recovery section to increase the urea content and remove at least a part of the unreacted ammonia and $CO_2$ from the urea solution;

Concentrating the urea solution from the recovery section by water evaporation in the evaporation section to give a urea melt and water vapor comprising urea and ammonia;

Condensing the water vapor in a condensation section to give process condensate comprising water, urea and ammonia.

In this embodiment, the process further comprises:

Preferably solidifying a first part of the urea melt in a finishing section using cooling air, e.g. a granulator or prilling tower, giving solid urea product and a waste air stream comprising urea and $NH_3$ as off-gas;

Preferably removing urea dust from the off-gas by dust scrubbing, upstream of the acid scrubbing, Acid scrubbing of off-gas from the urea production plant, preferably at least in part from the finishing section, and preferably after the dust scrubbing of the off-gas, with nitric acid in an acid scrubber yielding the acid aqueous ammonium nitrate stream and cleaned off-gas.

Preferably the process comprises: supplying a second part of the urea melt to the UAN production.

In a preferred embodiment, the acid scrubbing is used both for off-gas from the finishing section after dust scrubbing, and for off-gas from the urea production plant, e.g. from the synthesis section and recovery section.

Preferably the process comprises: treating the process condensate, in the waste water treatment (WWT) section, by supplying at least a part through a first desorber, a hydrolyser, and a second desorber, wherein said units are connected in series in said order by liquid flow lines.

In a preferred embodiment of the system, the system comprises these units and connections corresponding to said steps.

As a general preference for the process and the system, the ammonia solution used for the pH control (pH adjustment) step of the process is an untreated process condensate stream, or a partially treated process condensate stream from the wastewater treatment section of a urea plant, or combination thereof, for example with a composition, of 0.1-1.0 wt. % ammonia, 0.5-1.5 wt. % urea, max. 0.1 wt. % $CO_2$, and at least 90% water, preferably rest water. This provides various advantages, including easier joining of the streams in the pH control section, and a lower load of the WWT, more in particular a lower load of the hydrolyser, which an energy intensive unit using (medium pressure) steam.

Preferably, in said embodiment of the process with the step of treating the process condensate in the waste water treatment (WWT) section, the process comprises:

withdrawing ammonia solution, being untreated or partially treated process condensate, from one or more liquid flow lines selected from the group consisting of: the liquid flow line from the condensation section to the first desorber, the liquid flow line from the first desorber to the hydrolyser, and the flow line from the hydrolyser to the desorber; preferably at least in part or entirely from the liquid flow line from the first desorber to the hydrolyser; and using said ammonia solution in the pH control step, in particular in the pH adjustment step; wherein the ammonia solution preferably comprises 0.1-1.0 wt. % ammonia, 0.5-1.5 wt. % urea, max. 0.1 wt. % $CO_2$, and at least 90% water.

Herein, the hydrolyser is used to hydrolyse urea down to very low levels (ppm), with live steam, typically with medium pressure steam (15 to 25 bar).

The system preferably comprises a ammonia solution supply line for ammonia solution from a solution tap point to the pH control section, wherein the solution tap point is located in a flow line is selected from the group consisting of: the liquid flow line from the condensation section to the first desorber, the liquid flow line from the first desorber to the hydrolyser, and the flow line from the hydrolyser to the desorber. In the tap point, a part of the ammonia solution in the flow line is withdrawn into the ammonia solution supply line.

It will be understood that, in the process of the invention, the evaporation of the pH-controlled liquid, preferably by heating, will result in the formation of water vapors, e.g. a vapor stream comprising water vapor and entrained ammonium nitrate.

In a preferred embodiment of the process, these vapors are subjected to treatment as described above with reference to the system of the invention. Hence, the treatment section of the system can be used in this preferred embodiment of the process.

Accordingly, a preferred embodiment of the process comprises subjecting water vapor resulting from the evaporation of the pH-controlled liquid, to scrubbing, particularly to scrubbing with water. More preferably, to this end the process, in this preferred embodiment, is conducted in a system as substantially described hereinbefore and/or has the features as described in connection with the treatment section.

Also provided is a method for modifying a pre-existing chemical processing unit having an outlet for a waste acid aqueous ammonium nitrate stream. The method comprises providing a system for the production of urea ammonium nitrate (UAN) as discussed hereinabove, and connecting said outlet of the chemical processing unit such that the outlet for the waste acid aqueous ammonium nitrate to the inlet for acid aqueous ammonium nitrate of the system for the production of UAN. Hence in the modified plant, the acid aqueous ammonium nitrate stream is supplied from the outlet to the system, in particular to the pH control unit. The pre-existing chemical processing unit preferably comprises an acidic scrubber, as described hereinbefore in connection with the system.

In sum, a system and process are disclosed for the production of urea ammonium nitrate (UAN), which is particularly suitable for processing relatively small ammonium nitrate waste streams into UAN. The system comprises a concentration section for ammonium nitrate, a treatment section which allows recovering and recirculating nitrogen compounds entrained in vapor from the concentration section, and a pH control section allowing to adjust the pH of the processed ammonium nitrate waste stream to the extent necessary.

Figures The invention is hereinafter illustrated with reference to the following non-limiting discussion of the drawings.

FIG. 1 is a general schematic representation of a system for the production of urea ammonium nitrate (UAN) according to the invention. The system can be added to any plant or piping having an outlet for acid aqueous ammonium nitrate, particularly in the form of a used acid scrubbing liquid (also called first used scrubbing liquid). The system (1) comprises an inlet (101) for aqueous ammonium nitrate (121), an inlet (102) for liquid urea (122), and an outlet (103) for UAN (123). The aqueous ammonium nitrate (121) typically also contains nitric acid. The acid aqueous ammonium nitrate stream (121) is e.g. a first used scrub liquid.

The system comprises a concentration section (104), which is configured to subject aqueous ammonium nitrate to evaporation. The system is configured such that concentrated ammonium nitrate (125) resulting from said evaporation can be led to a UAN production section (105) configured to mix concentrated ammonium nitrate and liquid urea so as to produce UAN.

The concentration section has a gas outlet (106) for water vapor (126), e.g. for a vapor stream (gaseous stream) comprising water vapor. The vapor stream may also comprise nitric acid and entrained ammonium nitrate. Said gas outlet is in fluid communication with a treatment section (107). The treatment section is configured to subject water vapor received from the concentration section (126) to scrubbing, resulting in a cleaned vapor stream (127). To this end, said treatment section has an inlet (108) for treatment liquid (128) and an outlet (109) for used treatment liquid (129). The latter outlet (109) is preferably in fluid communication, in particular by a liquid flow line, with an inlet (110) of the concentration section (104).

In another embodiment, the outlet (109) for used treatment liquid (129) is in fluid communication, in particular by a liquid flow line, with an inlet of the UAN production section (105). For example, the used treatment liquid (129) is supplied directly to the UAN production section (105). However, an advantage of supplying the used treatment liquid to the inlet of the concentration section, relative to adding the used treatment liquid to the concentrated ammonium nitrate (125), is that the concentration section needs to evaporate water to a less degree, i.e. the ammonium nitrate can contain more water (wt. %) at the outlet of the concentration section, which is advantageous (energy efficiency, safety). Furthermore, the amount of treatment liquid (128) can be relatively large compared to the concentrated ammonium nitrate (125). In an example the amount of water in the treatment liquid (128) and in the used treatment liquid (129) is approximately 10× the amount of water in the concentrated ammonium nitrate (125). Adding such amount of water downstream of the concentration section would upset the water balance for the UAN production.

It is also possible that the used treatment liquid (129) is in part supplied to the concentration section (104) and in part supplied directly to the UAN production section (105). The used treatment liquid (129) corresponds to the second used scrub liquid (214) in FIG. 2.

In accordance with the invention, the system comprises a pH control section (111) such that the inlet for aqueous ammonium nitrate is in fluid communication with an inlet (112) of the pH control section. The pH control section is configured to subject aqueous ammonium nitrate to pH control. This control is preferably a feed-forward or feedback system for determining pH of the aqueous ammonium nitrate that has entered the section via said inlet (112), and for adjusting pH as necessary, so as to provide a pH-controlled aqueous ammonium nitrate stream (124). The pH control section has an outlet (113) for said pH-controlled aqueous ammonium nitrate stream, which is in fluid communication with the inlet (110) of the concentration section. The pH control section (111) preferably has a further inlet for an aqueous ammonia solution and a zone for mixing or combining the streams, e.g. with active or static mixing.

In a preferred embodiment wherein two liquid streams that are sent to the concentration section, i.e., the used treatment liquid (129) from the treatment section and the pH-controlled aqueous ammonium nitrate stream (124), these liquid streams for example enter said concentration section (104) via two distinct inlets. Whilst this is not shown in FIG. 1, it will be understood that also in the event that the two liquid streams concerned are not then being combined until within the concentration section, this still is based on the preferred feature of fluid communication between the inlet (110) of the concentration section (via which the pH-controlled aqueous ammonium nitrate stream enters the concentration section) and the outlet (109) for used treatment liquid from the treatment section, since the streams will be combined within the concentration section, thus implying fluid communication between the inlet of either fluid into the concentration section, and the corresponding outlets from the respective sections upstream of the concentration section (i.e., the pH-control section for the pH-controlled aqueous ammonium nitrate stream and the treatment section for the used treatment liquid therefrom).

In an alternative embodiment (not shown in FIG. 1), the outlet (109) for used treatment liquid has a direct liquid flow line to an inlet of the UAN production section (105), bypassing the concentration section (104). The treatment unit (107) is optional for the process.

In the process of the invention, the treatment unit (107) is optional.

FIG. 2 illustrates a process flow diagram for a non-limiting example of a UAN plant, consistent with one or more embodiments of the present disclosure. It illustrates an example embodiment of the system for the production of urea ammonium nitrate of the invention. Said UAN plant (i.e. the system) may receive an acid aqueous ammonium nitrate stream, in particular in the form of a first used scrubbing liquid stream (205), and process said first used scrubbing liquid stream (205) into a UAN product stream (211). In this example, first used scrubbing liquid stream (205) comes from acidic ammonia scrubbers in urea melt and granulation plant, where ammonia-containing gas stream (off-gas or waste air stream containing $NH_3$) is scrubbed with a first scrub liquid, which contains nitric acid.

The first used scrubbing liquid stream (205) has a flowrate of about 2000 kg/h and a composition of 10 wt. % of ammonium nitrate, 0.5 wt. % of nitric acid, and balancing amounts of water. UAN plant (226) comprises a pH control section (228) that may include a tie-in point at which ammonia needs to be added to first used scrubbing liquid stream (205) to adjust, i.e. increase, its pH at approximately 3.0. To this end, by way of non-limiting example, a small amount (2.3 kg/h) of $NH_3$ is injected into first used scrubbing liquid stream (205) (aqueous ammonium nitrate stream) via line (206a) through valve (231) to obtain a pH-controlled (in this example a pH-adjusted) first used scrubbing liquid stream (207) (i.e. pH-controlled aqueous ammonium nitrate stream) with a temperature of approximately 37° C. If pure ammonia in gas or liquid form are to be injected into first used scrubbing liquid stream (205), then valve (231) should be a very small, i.e. a lab-scale valve. In this case, valve (231) must be placed in a specially designed cabinet to be protected against harsh environment. Also, the valve typically needs to be positioned very close to the line carrying first used scrubbing liquid stream (205), which creates complications in the event of a lab-scale valve. To avoid such complications, and generally to permit the use of conventional industrial valves, an ammonia solution is injected via line (206a) through valve (231) into first used scrubbing liquid stream (205), wherein the ammonia solution may have an ammonia content of 0.5 wt. %, which allows for providing the required 2.3 kg/h $NH_3$ at a higher flow rate and therefore valve (231) may be a normal sized industrial valve.

In this example (and as shown in more detail in FIG. 4), and as a general preference, the ammonia solution used for the pH control (pH adjustment) is a partially treated condensate stream from the wastewater treatment section of a urea plant, for example with a composition, of 0.1-1.0 wt. % ammonia, 0.5-1.5 wt. % urea, and max. 0.1 wt. % $CO_2$, rest water. A non-limiting example composition is 0.5 wt. % ammonia, 0.8 wt. % urea, 0.09 wt. % $CO_2$, and balancing amounts of water. Utilizing a stream with this composition, instead of injecting a very small amount of pure ammonia eliminates the need for designing special equipment such as lab-scale valves. Specifically, when using an ammonia solution with an ammonia content of 0.5 wt. % by injecting 460 kg/h of such ammonia solution, the required amount of 2.3 kg/h $NH_3$ for pH adjustment is met. This means that valve (231) is handling a flowrate of 460 kg/h instead of 2.3 kg/h. This advantage is obtained by using ammonia solution with 0.1-1.0 wt. % ammonia, 0.5-1.5 wt. % urea, and max. 0.1 wt. % $CO_2$, rest water. An ammonia solution with this composition is very elegantly provided by a partially treated condensate stream from the wastewater treatment section of a urea plant.

The pH-adjusted first used scrubbing liquid stream (207) is then sent to a concentration section comprising an evaporator (230). In this example, evaporator (230) is a vertical-one-pass (VOP) type evaporator and may be operated at about atmospheric conditions or slightly under vacuum and is heated by 3.5 bara pressure steam to a temperature of about 128° C. The evaporator is hence a heat exchanger. The discharge of the evaporator (230) is flashed into a first vapor stream (209) and a concentrated ammonium nitrate solution stream (208). The concentrated ammonium nitrate solution stream (208) has, as a non-limiting example, a concentration of 76 wt. %, a temperature of 128° C., and a pH of 2.0. The concentrated ammonium nitrate solution stream is sent to a UAN production section (232). This UAN production section includes a UAN mixing tank (236) where a urea stream (210a), in particular a diluted urea melt stream (210a) is mixed with the concentrated ammonium nitrate stream (208) and, downstream thereof and in fluid communication therewith, a circulation cooler (238), where the produced UAN is cooled down to 40° C. The urea stream (210a) is preferably obtained by combining urea melt (210) with an aqueous stream (242), e.g. process condensate, as discussed hereinafter.

The first vapor stream (209) contains 220 ppm of $HNO_3$ and 210 ppm of AN (molar ppm), which are considered undesirable entrainments that are to be separated from such first vapor stream (209) before this stream can be either vented or condensed and reused.

By way of non-limiting example, treatment unit (234) is a trayed scrubbing column with a 1 m diameter and a specific liquid loading of 0.5 $m^3/m^2h$, in which a condensate stream (213), i.e. essentially pure water, is used as scrubbing liquid (second scrubbing liquid) that is brought into contact with said first vapor stream (209) over the trays of treatment unit (234). Based on the diameter and the specific liquid loading of trays, a flow rate of approximately 400 kg/h of condensate (213) is sent to the top of treatment unit (234) and scrubs off entrained $HNO_3$ and AN from the first vapor stream (209) as it flows down to obtain a cleaned first vapor stream (212) and a used treatment liquid, herein called the second used scrubbing liquid (214). Here, the second used scrubbing liquid (214) contains nitric acid and ammonium nitrate entrainments and has a temperature of approximately 100° C. In the illustrated example, the second used scrubbing liquid (214) is recycled back to an inlet of evaporator (230) and it is mixed with the aforementioned pH-adjusted first scrubbing liquid (207) upstream the evaporator (230). This increases the temperature of pH-adjusted first scrubbing liquid from 37° C. to 55° C., such that heat is recovered.

In this example (FIG. 2), a urea melt stream (210) with a concentration of 96 wt. % and a temperature of 135° C. is drawn from the first stage evaporator in the urea melt plant and then is diluted down to a concentration of 79 wt. % by adding process condensate to it by process condensate stream (242). Then, diluted urea melt stream (210a) is sent to UAN production section (232) to be mixed with the concentrated ammonium nitrate stream (208). The urea melt line that carries urea melt from the urea melt plant to the UAN plant in this example is a long line of 100 meters with a small diameter of 1 inch (2.5 cm). If urea melt at a high temperature and concentration is transported in such long line, there is a high chance for biuret formation. Furthermore, urea melt is taken at 135° C., while at a concentration of 96 wt. %, the crystallization occurs at 130° C., therefore there is a high chance of crystallization in such long line. By adding water, e.g. as the process condensate, the urea melt is diluted down to 79 wt. % and also its temperature is reduced, and therefore the risk of crystallization is eliminated. The added process condensate is e.g. process condensate withdrawn from the condensation section of the urea plant, i.e. prior to treatment of that condensate in the WWT; this untreated condensate may advantageously contain some $NH_3$.

Figure 3:
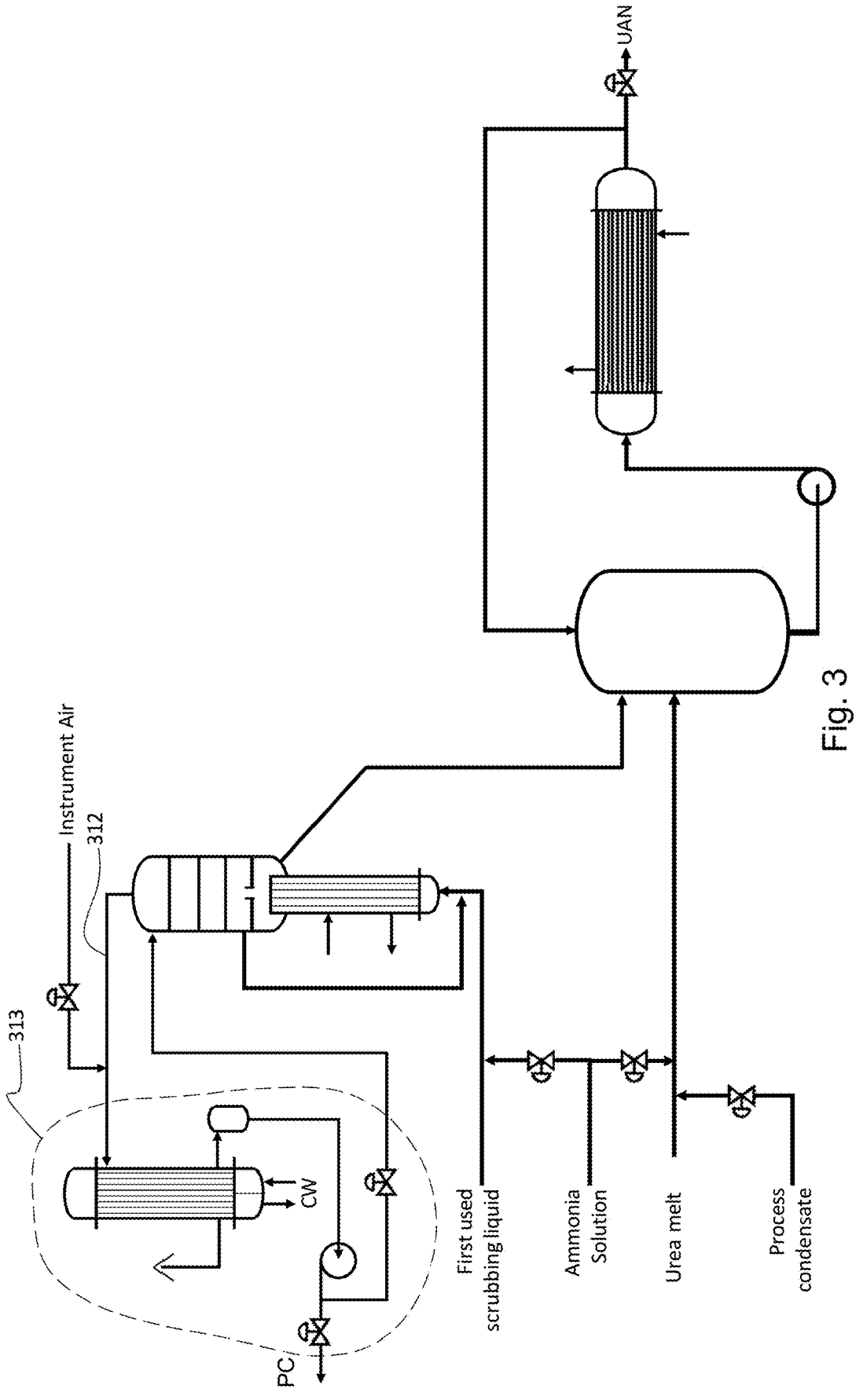

FIG. 3 is based on the flow scheme of FIG. 2, in an embodiment having the following addition. The cleaned first vapor stream (312) is sent to a condensation unit (313) and at least a portion of the resulting condensate may be recycled back to treatment unit (234) as the scrubbing liquid. For example, at least a portion of the condensate is not added to the first used scrubbing liquid stream in the flow line from the acid scrubber; thereby the first used scrubbing liquid is concentrated in the concentration section.

Figure 4:
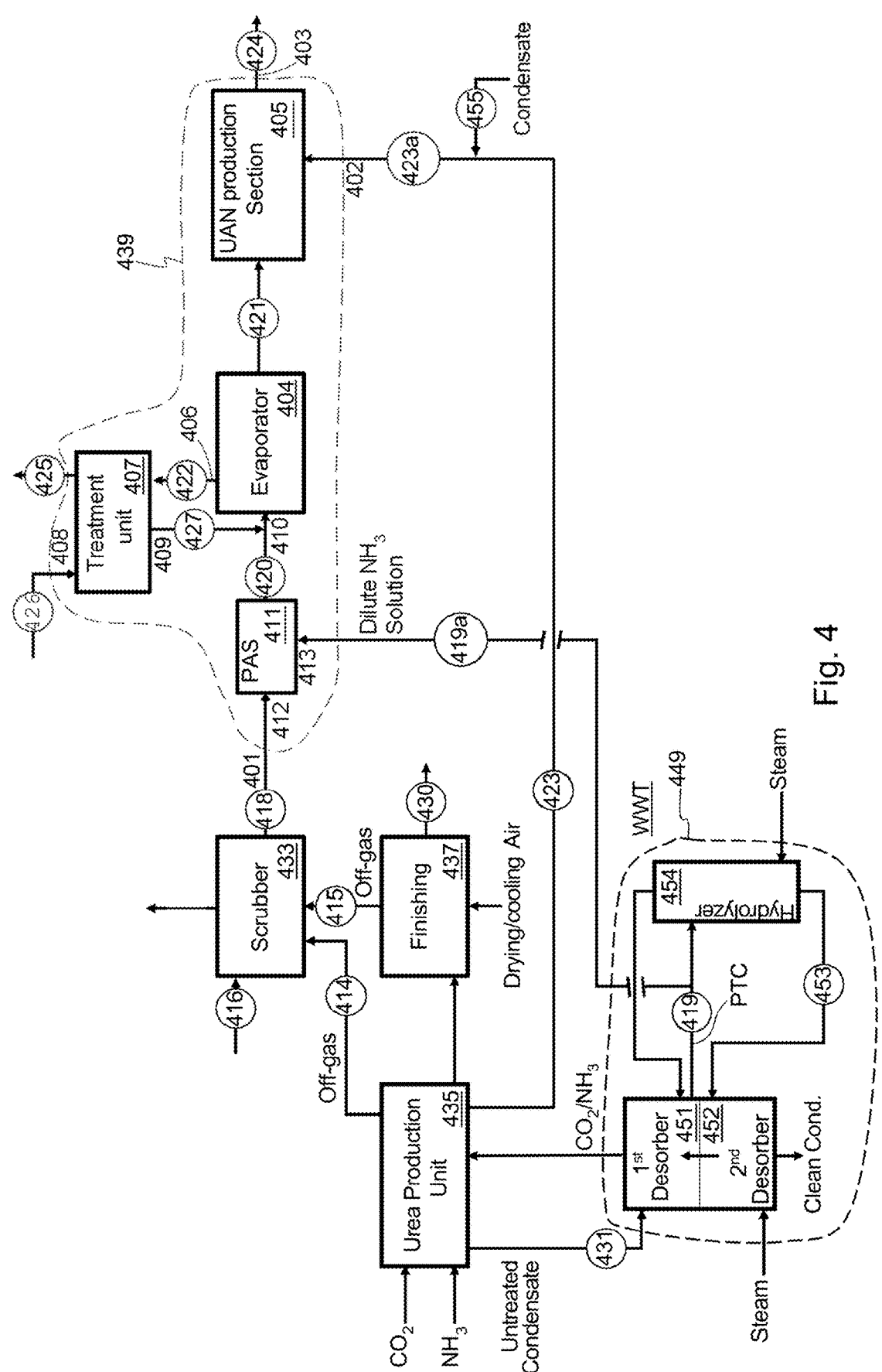
FIG. 4 represents a process flow diagram for a system for the production of urea ammonium nitrate (UAN) according to the invention, wherein the process is integrated with a urea production process.

FIG. 4 represents a process flow diagram for a system for the production of urea ammonium nitrate (UAN) according to the invention, wherein the process is integrated with a urea production process. The corresponding systems include a system (439) for the production of urea ammonium nitrate (UAN) according to the invention. This system comprises, in analogy as described for the system of FIG. 1, comprises:

(401) an inlet for aqueous ammonium nitrate;
    (402) an inlet for liquid urea;
    (403) an outlet for UAN;
    (404) a concentration section;

(405) a UAN production section;
(406) a gas outlet (106) for water vapor;
(407) a treatment section configured for scrubbing water vapor;
(408) an inlet for treatment liquid;
(409) an outlet for used treatment liquid;
(410) an inlet of the concentration section;
(411) a pH control section;
(412) an inlet to the pH control section;
(413) an inlet for dilute aqueous ammonia solution for pH-control.

In a non-limiting example of the process, a first off-gas stream (414) is an ammonia-containing off-gas stream resulting from the production of a urea solution in a urea production unit (435); a second off-gas stream (415) is an ammonia-containing off-gas resulted from solidification of a urea solution in a finishing section (437). The first respectively second off-gas stream may also be used alone.

Ammonia within the ammonia-containing off-gas streams is allowed to react with nitric acid in an acidic ammonia scrubber (433) to form ammonium nitrate salt, which remains dissolved in water (AN solution), with residual nitric acid also being present. For example, as an embodiment for the system of the invention in general, said acidic ammonia scrubber (433) may include, e.g., a packed bed or trays, and ammonia may react with nitric acid over said packed bed of said acidic ammonia scrubber. The AN solution is discharged from the acidic ammonia scrubber, resulting in a first used scrubbing liquid stream, i.e., an acid aqueous ammonium nitrate stream (418), also containing nitric acid. For example, as an embodiment for the system of the invention in general, a scrubbing unit with two different compartments may be utilized, where in one compartment dust is removed from the off-gas streams and then dust-scrubbed off-gas is sent to another compartment, which is configured similar to said acidic ammonia scrubber (433), where ammonia content is reduced by utilizing a nitric acid solution. For example, a typical scrubbing unit in a urea production/solidification plant may include a lower dust scrubbing compartment and an upper acidic scrubbing compartment; in said lower compartment (dust scrubber) a urea solution of, e.g., about 45 wt. % is circulated to remove the urea dust from the off-gas. After leaving said lower compartment, the off-gas is introduced into said upper compartment where the ammonia content is reduced by means of a nitric acid solution. The ammonia reacts with nitric acid to form ammonium nitrate. The ammonium nitrate solution is circulated over the ammonia scrubber before being sent out to the battery limits. The circulation is maintained by means of an ammonia scrubber circulation pump. Fresh nitric acid (416) is supplied to maintain the acidity of the circulating solution. In an example, said first used scrubbing liquid (418) may have a flow rate of approximately 2000 kg/h and may contain 5-20 wt. % of ammonium nitrate, 0.1-2 wt. % of nitric acid, 0.1 to 1.0 wt. % urea, and a balancing amount of water. The pH of the first used scrubbing liquid (418) may be in a range of 0.5 to 1.8 based on its nitric acid content.

The aqueous ammonium nitrate stream, i.e., said first used scrubbing liquid (418), which is typically a small waste stream, is sent to a UAN plant (439) (or UAN production section), i.e., a system according to the invention, designed for processing said small ammonium nitrate waste stream to UAN. In the UAN plant (439), the pH of the aqueous ammonium nitrate stream (418) is first adjusted by dosing an ammonia solution (419a) into said aqueous ammonium nitrate stream (418) in a pH control section, in particular the pH adjustment section (411). The ammonia solution (419a)

may include, e.g., an aqueous ammonia solution with a concentration in a range of 0.5 to 5 wt. %. The pH adjustment section (PAS) (411) may comprise, e.g., a static mixer where ammonia solution (419a) may be mixed in with the aqueous ammonium nitrate stream (418). Or, alternatively, the pH adjustment section (411) may be a tie-in point where the ammonia solution (419a) is injected into the aqueous ammonium nitrate stream (418). Said ammonia solution (419a) is for example an ammonia-containing stream with an ammonia concentration of, e.g., at most 10 wt. %. For example an untreated condensate (431) from a urea production unit (435), or a partially treated condensate streams (419, 453) from a wastewater treatment section (449) can be used, as discussed below. In another example, said ammonia solution (419a) may be a dilute urea solution with an ammonia content of at most 10 wt. %.

The pH of the aqueous ammonium nitrate stream (418) may be adjusted, i.e. increased, to a slightly acidic range in said pH adjustment section (411), thereby obtaining a pH-adjusted aqueous ammonium nitrate stream (420). This stream has a pH generally in the range of 2.0 to 4.5. The flow rate ratio of said ammonia solution (419a) to the aqueous ammonium nitrate stream (418) may be controlled in a feed forward control loop.

The pH-adjusted aqueous ammonium nitrate stream (420) is subjected to evaporation in a concentration section (404) to obtain a concentrated ammonium nitrate solution (421) and a first vapor stream (422). Said concentrated ammonium nitrate solution (421) preferably has a concentration of at most 75 wt. % or at most 80 wt. %, considering safety issues associated with higher concentrations of ammonium nitrate solution.

The concentration section (404) generally comprises an evaporator. This may be a vertical-one-pass (VOP) type evaporator, and may be operated at about atmospheric conditions or slightly under vacuum and at a temperature of about 125-140° C. Heating medium can be low pressure saturated steam with a pressure of approximately 3.5 bara.

Said concentrated ammonium nitrate solution (421) with a concentration of 75-80 wt. % is then combined with an aqueous urea solution and/or a urea melt (423a) in a UAN production section (405) to obtain a urea ammonium nitrate solution (424). For example, thereby the concentrated ammonium nitrate solution (421) may be combined with a urea solution or a diluted urea melt stream (423a) in said UAN production section (405). As an example of a general embodiment of the invention, such diluted urea melt stream (423a) may be obtained by diluting a urea melt stream (423) from an evaporation stage in a urea production unit (435). For example, a urea melt stream from the evaporation stage of urea production unit (435), such as urea melt stream (423) that may have a 90-96 wt. % concentration is diluted to about 79 wt. % by adding water, e.g. as a process condensate (455), to urea melt stream (423) upstream said UAN production section (405); in particular at a position close to the evaporation section of the urea production plant and relatively far away, e.g. at least 50 m, from the UAN production section (FIG. 4 is schematic in this respect). Such dilution may be carried out to reduce the residence time, minimizing the biuret formation and to reduce the chance of crystallization within the melt line.

Said diluted urea melt stream (423a) is e.g. obtained by adding an aqueous stream to a urea melt stream with a urea concentration in a range of 70-98.5 wt. %. The diluted urea melt stream (423a) preferably comprises 70-85 wt. % urea.

The urea production unit (435) comprises, in addition to a synthesis section and a recovery section, an evaporation section. The evaporation section for example may include, e.g., two evaporation stages. In this case, a urea melt stream (423) may be from the first stage evaporator, such that urea melt concentration is between 90 wt. % and 96 wt. % at most. In practice, the aforementioned process condensate (455) is added to urea melt stream (423) close to the urea melt pump. A melt line between urea production unit (435) and UAN production section (405) can be a long line with a length of, for example, approximately 100 meters and therefore there is a risk of biuret formation within the melt line, by adding said process condensate (455) the temperature is reduced and biuret formation is minimized.

The urea ammonium nitrate solution (424) may further be cooled down to, e.g., 40° C. and then sent to battery limits via a UAN export pump. As an embodiment of the invention in general, a requested UAN grade can be achieved by keeping the ratio of AN/urea in a mixing tank of the UAN production section (405) at a given value calculated based on the UAN grade. For example, in case of UAN-32, the ratio of AN/urea in the mixing tank of UAN production section (435) may be kept at about 1.33 (mass ratio) and by adjusting the condensate to have a 20 wt. % water in the final urea ammonium nitrate solution (424). However, other UAN grades such as UAN-28 or UAN-30 may also be produced by adjusting the ratio of AN/urea and the cooled steam condensate.

The aforementioned first vapor stream (422) coming from the evaporator (404), which contains a certain entrainment of $HNO_3$ and AN of the order of 200-300 ppm-mol, is treated in a treatment unit (407) to obtain a cleaned first vapor stream (425) by separating entrained ammonium nitrate and nitric acid from said first vapor stream (422). As a general embodiment of the invention, the treatment unit (407) may include, e.g., a scrubber that allows for scrubbing said first vapor stream (422) with a condensate stream (426) as the treatment liquid to obtain said cleaned first vapor stream (425) and a used treatment liquid (427), also called second used scrubbing liquid stream, that contains ammonium nitrate and nitric acid separated from the first vapor stream that contained entrained ammonium nitrate and nitric acid (422). For example, the treatment unit (407) may include a scrubber equipped with trays or packing and/or a demister. The flowrate of condensate stream (426) may be determined based on the specific liquid load of the trays and the scrubber column diameter. In an example, the treatment unit (407) may include a scrubbing column with a diameter of 1 m and a specific liquid loading of 0.5 $m^3/m^2h$. Here the flowrate of the condensate stream (426) entering the top of treatment unit (407) may be, e.g., about 400 kg/h. This condensate stream (426) may scrub the retained ammonium nitrate and nitric acid out of the first vapor stream (422). Then, the used treatment liquid stream (427) containing nitric acid and ammonium nitrate from the bottom of the scrubber and is, for example, recycled to the inlet of the condensation section (404). Separating this second used treatment liquid stream (427) by having an outlet for it that is separate from the outlet for the concentrated ammonium nitrate solution (421) (also in embodiments wherein the treatment unit 407 is mounted directly on top of the evaporator 404) is preferred in order to prevent diluting the concentrated ammonium nitrate solution (421) that is to be introduced into the UAN production section (405).

In an example, ammonia solution (419a) may include an ammonia-containing stream with a composition of 0.5 wt. % $NH_3$ at a temperature of 140° C. The ammonia solution (419a) may be supplied from a wastewater treatment section (449) that may be operatively connected to a production unit, such as urea production unit (435) to receive an untreated ammonia-containing condensate stream (431). The $NH_3$ concentration in the untreated ammonia-containing condensate stream (431) may be about 5 wt. %; the condensate stream (431) may also comprise urea. In the wastewater treatment section (449), untreated ammonia-containing condensate stream (431) may be passed through a desorption column (451) to obtain a partially treated condensate stream (419) that contains at least 0.5 wt. % ammonia and that may be considered a dilute ammonia solution. Then, a small portion of the partially treated condensate stream (419) may be routed to the UAN plant (439) as ammonia solution (419a). Alternately, at least a portion of the untreated ammonia-containing condensate stream (431) may also be sent to the UAN plant (439) as an ammonia solution (419a).

The wastewater treatment section (449) may include, e.g., a desorption unit made up of a $1^{st}$ desorber (451) and a $2^{nd}$ desorber (452), and a hydrolyzer (454). In an example, said $1^{st}$ desorber (451) may operate at, e.g., about 3.6 bar and the bulk of the ammonia within untreated ammonia-containing condensate stream (431) may be stripped off by means of the overhead vapors of the $2^{nd}$ desorber (452) and the hydrolyzer (454). The aforementioned partially treated condensate stream (419) is actually a bottom effluent of said $1^{st}$ desorber (451) which is pumped to the top of the hydrolyzer (454) via a heat exchanger, where partially treated condensate stream (419) is heated from approximately 140° C. to 190° C. In the hydrolyzer (454), the urea within the partially treated condensate stream (419) is decomposed into ammonia and carbon dioxide while being heated by means of live high-pressure steam, to about 200-210° C. To obtain very small urea concentrations in the hydrolyser effluent (453) (about 1 ppm-wt.), partially treated condensate stream (419) is counter-currently contacted with the live steam. The hydrolyzer (454) operates at about 16 bar. The hydrolyzer effluent (453), containing traces of urea, goes via the hydrolyser heat exchanger to the top of the $2^{nd}$ desorber (452). The overhead vapor of the hydrolyser is sent to the bottom of the $1^{st}$ desorber (451). After cooling the hydrolyser effluent (453) in the hydrolyser heat exchanger to about 149° C., the hydrolyser effluent (453) is fed to the top of the $2^{nd}$ desorber (451). Here, the remaining ammonia and carbon dioxide is stripped off by means of live low-pressure steam. The process condensate, leaving the desorber, is cooled in the desorber heat exchanger. It contains very small amounts of urea and ammonia (about 1 ppm-wt. ammonia and about 1 ppm-wt. urea) and can be used for several purposes i.e., for boiler feed water or cooling water make up. As mentioned before, the untreated condensate stream (431), the partially treated condensate stream (419), and/or the hydrolyzer effluent (453) may be utilized as ammonia solution stream (419a).

In embodiment of the process, the process comprises scrubbing off-gas in scrubber (433) to give the acid aqueous ammonium nitrate (418), and supplying it to pH adjustment (411) by adding ammonia solution, evaporation in evaporator (404) and UAN production (405), with the further steps and units being optional. In the process, the treatment (407) of the vapor (422) from the evaporator (404) is preferred. As a further preference for the process, the used treatment liquid (427) is supplied to the inlet of the evaporator (404). As an independent preference for the process, the ammonia solution (419a) used for the pH adjustment originates from the liquid flow line (419) between the first desorber (451) and the hydrolyser (454). As a further independent preference for the process, the UAN production (405) receives urea solution (402) that is diluted by adding water (455) to a urea melt (423) . . . .

The term 'may' indicates example, optional or preferred features; other configurations than the specified configuration are also possible.

Preferences and details for the system also apply for the process, and vice versa. In particular composition and pH levels discussed in the context of the system, are also applicable to the process. The process of the invention is for example, but not exclusively, carried out in the system of the invention. The system is preferably suitable for carrying out the process.

The 'system' of the invention can also be referred to as an 'apparatus' or 'plant'.

Where reference is made to the system comprising a unit A in fluid communication with a unit B or with an inlet or outlet of unit B, the system preferably comprises unit A and B.

Fluid communication of a gas inlet or gas outlet indicates a gas flow line, i.e. a flow line for gas. Fluid communication of a liquid inlet or outlet indicates a liquid flow line, i.e. a flow line for liquid.

The invention claimed is:

1. A process for the production of urea ammonium nitrate (UAN), comprising obtaining an acid aqueous ammonium nitrate stream resulting as a used scrubbing liquid from subjecting an ammonia-containing off-gas to contact with nitric acid in a scrubber; subjecting the acid aqueous ammonium nitrate stream to a pH controlling step, said pH controlling step comprising determining pH and adjusting pH to the extent necessary so as to be within a range of 2 to 4.5 so as to provide a pH-controlled liquid, subjecting said pH-controlled liquid to evaporation so as to obtain a concentrated ammonium nitrate solution and combining said concentrated ammonium nitrate solution and an aqueous urea solution and/or a urea melt so as to obtain a urea ammonium nitrate solution, wherein the acid aqueous ammonium nitrate stream comprises:

5-20 wt. % of ammonium nitrate;
less than 5 wt. % urea, and
0.1-0.5 wt. % nitric acid.

2. A process according to claim 1, wherein the pH controlling step comprises adding an aqueous ammonia solution comprising at most 5 wt. % of ammonia.

3. A process according to claim 1, wherein the concentrated ammonium nitrate solution has a concentration of 75 to 80 wt. %.

4. A process according to claim 1, comprising subjecting water vapor resulting from the evaporation of the pH-controlled liquid, to scrubbing.

5. A process according to claim 1, comprising conducting the process in a system for the production of urea ammonium nitrate (UAN) comprising an inlet for aqueous ammonium nitrate, an inlet for liquid urea, and an outlet for UAN, the system comprising a concentration section configured to subject aqueous ammonium nitrate to evaporation, so as to provide concentrated ammonium nitrate and, downstream of the concentration section and in fluid communication therewith, a production section configured to mix concentrated ammonium nitrate and liquid urea so as to produce UAN, wherein the concentration section has a gas outlet for water vapor, said gas outlet being in fluid communication with a treatment section configured to subject water vapor received from the concentration section to scrubbing, said treatment section having an inlet for scrubbing liquid and an outlet for used scrubbing liquid, wherein the outlet for used scrubbing liquid is in fluid communication with an inlet of the concentration section, and wherein the system comprises a pH control section such that the inlet for aqueous ammonium nitrate is in fluid communication with an inlet of the pH control section, wherein the pH control section is configured to subject aqueous ammonium nitrate to pH control, so as to provide a pH-controlled aqueous ammonium nitrate stream, wherein the pH control section has an outlet for the pH-controlled aqueous ammonium nitrate stream in fluid communication with an inlet of the concentration section; wherein the pH controlled liquid is subjected to evaporation in the concentration section and the concentrated ammonium nitrate solution and an aqueous urea solution and/or a urea melt are combined in the production section.

6. A process according to claim 1, wherein said off-gas contains air and said off-gas is counter-current contacted with nitric acid containing liquid in said scrubber.

7. A process according to claim 1, wherein the step of obtaining the acid aqueous ammonium nitrate stream comprises: subjecting a urea melt to solidification in a finishing section, using cooling air to provide a solid urea product and a waste air stream comprising urea dust and $NH_3$ and supplying the waste air stream, after dust scrubbing, as at least part of said off-gas processed in said scrubber.

8. A process according to claim 1, wherein at least 90 wt. % of the ammonium nitrate in the UAN originates from the acid aqueous ammonium nitrate stream.

9. A process according to claim 1, wherein at least 90 wt. % of the urea comprised in the UAN is added to the concentrated ammonia nitrate solution.

10. A process according to claim 1, wherein the aqueous urea solution and/or a urea melt originates from an evaporation section of a urea plant and contains $NH_3$.

11. A process according to claim 1, wherein a part of a urea melt containing at least 90 wt. % urea including biuret is diluted to form a diluted urea liquid stream with a concentration of 60-85 wt. % urea including biuret by adding an aqueous stream, and the resulting diluted urea liquid stream is combined with the concentrated AN solution for making the UAN.

12. A process according to claim 1, wherein the step of obtaining the acid aqueous ammonium nitrate stream comprises:

producing urea melt in a urea production plant comprising a synthesis section, a recovery section, an evaporation section, a condensation section, and a waste water treatment section, by said producing of urea melt comprising:

reacting $CO_2$ and $NH_3$ to form a urea solution in the synthesis section;

treating the urea solution from the synthesis section in the recovery section to increase the urea content and remove at least a part of the unreacted ammonia and $CO_2$ from the urea solution;

concentrating the urea solution from the recovery section by water evaporation in the evaporation section to give a urea melt and water vapor comprising urea and ammonia;

solidifying a first part of the urea melt in a finishing section using cooling air, e.g. a granulator or prilling tower, giving solid urea product and a waste air stream comprising urea and $NH_3$ as off-gas; and acid scrubbing of off-gas from the urea production plant, preferably at least in part from the finishing section, with nitric acid in an acid scrubber yielding the acid aqueous ammonium nitrate stream and cleaned off-gas, and supplying a second part of the urea melt to the UAN production.

13. The process according to claim 12 comprising:

condensing the water vapor in a condensation section to give process condensate comprising water, urea and ammonia; and treating the process condensate, in the waste water treatment (WWT) section, by supplying at least a part through a first desorber, a hydrolyser, and a second desorber, wherein said units are connected in series in said order by liquid flow lines, wherein the process further comprises:

withdrawing ammonia solution, being untreated or partially treated process condensate, from one or more liquid flow lines selected from the group consisting of: the liquid flow line from the condensation section to the first desorber, the liquid flow line from the first desorber to the hydrolyser, and the flow line from the hydrolyser to the desorber; and using said ammonia solution in said step of adjusting pH.

14. The process according to claim 2, wherein the pH controlling step comprises adding an aqueous ammonia solution comprising between 0.5 and 5 wt. % of ammonia.

15. The process according to claim 1, wherein the acid aqueous ammonium nitrate stream comprises:

5-15 wt. % of ammonium nitrate, at least 80 wt. % water;

less than 1.0 wt. % urea, and 0.1-0.5 wt. % nitric acid.

16. The process according to claim 12, further comprising removing urea dust from the off-gas by dust scrubbing, wherein the dust scrubbing is conducted upstream of the acid scrubbing of the off-gas.

17. The process according to claim 12, wherein the off-gas from the urea production plant originates at least in part from the finishing section.

18. The process of claim 12, wherein the second part of the urea melt is supplied as part of a diluted urea-containing liquid to the UAN production.

19. The process according to claim 13, wherein the ammonia solution is withdrawn at least in part or entirely from the liquid flow line from the first desorber to the hydrolyser.

20. The process according to claim 13, wherein the ammonia solution comprises 0.1-1.0 wt. % ammonia, 0.5-1.5 wt. % urea, max. 0.1 wt. % $CO_2$, and at least 90% water.

* * * * *